(12) United States Patent
Holley

(10) Patent No.: US 7,665,150 B2
(45) Date of Patent: Feb. 23, 2010

(54) DOUBLE-CUFFED CHEMOTHERAPY GLOVES

(75) Inventor: Steven Holley, West Roxbury, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 67 days.

(21) Appl. No.: 11/903,582

(22) Filed: Sep. 24, 2007

(65) Prior Publication Data

US 2009/0077701 A1    Mar. 26, 2009

(51) Int. Cl.
*A41D 13/08*    (2006.01)
(52) U.S. Cl. .................... 2/16; 2/162; 2/168; 2/161.7; 2/161.6
(58) Field of Classification Search ............... 2/162, 2/168, 161.7, 161.6, 165, 170, 917
See application file for complete search history.

(56) References Cited

U.S. PATENT DOCUMENTS

| | | | |
|---|---|---|---|
| 1,534,208 A * | 4/1925 | Gibson | 239/288 |
| 1,597,042 A * | 8/1926 | Beebe | 2/162 |
| 1,633,300 A * | 6/1927 | Wetzstein | 2/158 |
| 4,399,567 A * | 8/1983 | Weon Joong | 2/161.6 |
| 4,853,978 A | 8/1989 | Stockum | |
| 4,881,277 A | 11/1989 | Hogle | |
| 4,901,372 A | 2/1990 | Pierce | |
| 4,919,966 A | 4/1990 | Shlenker | |
| 4,935,260 A | 6/1990 | Shlenker | |
| 4,942,626 A | 7/1990 | Stern et al. | |
| 5,014,362 A | 5/1991 | Tillotson et al. | |
| 5,019,096 A | 5/1991 | Fox, Jr. et al. | |
| 5,031,245 A | 7/1991 | Milner | |
| 5,036,551 A | 8/1991 | Dailey et al. | |
| 5,039,750 A | 8/1991 | Miller et al. | |
| 5,045,341 A | 9/1991 | Shlenker | |
| 5,088,125 A | 2/1992 | Ansell et al. | |
| 5,089,205 A | 2/1992 | Huang et al. | |
| 5,128,168 A | 7/1992 | Shlenker et al. | |
| 5,130,159 A | 7/1992 | Shlenker et al. | |
| 5,138,719 A | 8/1992 | Orlianges et al. | |
| 5,180,605 A | 1/1993 | Milner | |
| 5,181,276 A | 1/1993 | Kersten et al. | |
| 5,236,703 A | 8/1993 | Usala | |
| 5,272,771 A | 12/1993 | Ansell et al. | |
| 5,317,759 A | 6/1994 | Pierce | |
| 5,335,373 A | 8/1994 | Dangman et al. | |
| 5,338,565 A | 8/1994 | Shlenker et al. | |
| 5,357,636 A | 10/1994 | Dresdner, Jr. et al. | |
| 5,399,400 A | 3/1995 | Nile et al. | |
| 5,438,709 A | 8/1995 | Green et al. | |
| 5,458,588 A | 10/1995 | Amdur et al. | |
| 5,459,879 A | 10/1995 | Fuchs | |
| 5,459,880 A | 10/1995 | Sakaki et al. | |
| 5,483,697 A | 1/1996 | Fuchs | |

(Continued)

*Primary Examiner*—Gary L Welch
*Assistant Examiner*—Alissa J Tompkins
(74) *Attorney, Agent, or Firm*—Elizabeth A. O'Brien, Esq; Lawrence A. Chaletsky, Esq

(57) ABSTRACT

A disposable elastomeric glove has a secondary cuff disposed distally of a primary cuff on a wrist region of the glove. The secondary cuff may be grasped by an opposite hand to safely remove the glove with the primary cuff in place to protect the skin on the wrist from contaminants on the opposite hand. The secondary cuff approximates the design of the primary cuff such that the removal process is similar to that of a conventional glove.

14 Claims, 2 Drawing Sheets

U.S. PATENT DOCUMENTS

| | | |
|---|---|---|
| 5,534,350 A | 7/1996 | Liou |
| 5,545,451 A | 8/1996 | Haung et al. |
| 5,549,924 A | 8/1996 | Shlenker et al. |
| 5,570,475 A | 11/1996 | Nile et al. |
| 5,571,219 A | 11/1996 | Gorton |
| 5,636,382 A | 6/1997 | Chopko et al. |
| 5,644,798 A | 7/1997 | Shah |
| 5,649,326 A | 7/1997 | Richard, Jr. et al. |
| 5,650,225 A | 7/1997 | Dutta et al. |
| RE35,616 E | 9/1997 | Tillotson et al. |
| 5,670,263 A | 9/1997 | Gazeley |
| 5,679,399 A | 10/1997 | Shlenker et al. |
| 5,691,069 A | 11/1997 | Lee |
| 5,709,672 A | 1/1998 | Illner |
| 5,742,943 A | 4/1998 | Chen |
| 5,780,112 A | 7/1998 | Pugh et al. |
| 5,817,365 A | 10/1998 | Richardson et al. |
| 5,817,433 A | 10/1998 | Darras |
| 5,881,386 A | 3/1999 | Horwege et al. |
| 5,881,387 A | 3/1999 | Merovitz et al. |
| 5,965,276 A | 10/1999 | Shlenker et al. |
| 5,974,589 A | 11/1999 | Pugh et al. |
| 5,985,955 A | 11/1999 | Bechara et al. |
| 5,993,923 A | 11/1999 | Lee |
| 5,997,969 A | 12/1999 | Gardon |
| 6,000,061 A | 12/1999 | Taneja et al. |
| 6,012,169 A | 1/2000 | Nishi et al. |
| 6,016,570 A | 1/2000 | Vande Pol et al. |
| 6,021,524 A | 2/2000 | Wu et al. |
| 6,051,320 A | 4/2000 | Noecker et al. |
| 6,106,889 A | 8/2000 | Beavers et al. |
| 6,119,272 A | 9/2000 | Tebbe |
| 6,143,416 A | 11/2000 | Brindle et al. |
| 6,175,962 B1 | 1/2001 | Michelson |
| 6,195,805 B1 | 3/2001 | Bourne et al. |
| 6,253,383 B1 | 7/2001 | Mallernee et al. |
| 6,329,444 B1 | 12/2001 | McGlothlin et al. |
| 6,345,394 B1 | 2/2002 | Nakamura et al. |
| 6,347,408 B1 | 2/2002 | Yeh |
| 6,347,409 B1 | 2/2002 | Nile et al. |
| 6,352,666 B1 | 3/2002 | Nile et al. |
| 6,365,278 B1 | 4/2002 | Hoerner et al. |
| 6,370,694 B1 | 4/2002 | Michelson |
| 6,378,137 B1 | 4/2002 | Hassan et al. |
| 6,383,552 B1 | 5/2002 | Noecker et al. |
| 6,391,409 B1 | 5/2002 | Yeh et al. |
| 6,523,181 B2 * | 2/2003 | Medves ..................... 2/161.6 |
| 6,560,782 B2 | 5/2003 | Hourihan et al. |
| 6,566,435 B1 | 5/2003 | Teoh et al. |
| 6,582,788 B2 | 6/2003 | Yeh |
| 6,684,405 B2 | 2/2004 | Lezdey |
| 6,730,380 B2 | 5/2004 | Littleton et al. |
| 6,749,859 B2 | 6/2004 | Leibowitz |
| 6,759,473 B1 | 7/2004 | Nakamura et al. |
| 6,775,848 B2 | 8/2004 | McGlothlin et al. |
| 6,805,963 B2 | 10/2004 | Janssen et al. |
| 6,874,165 B2 | 4/2005 | Lee |
| 6,895,600 B2 | 5/2005 | Williams |
| 6,913,758 B2 | 7/2005 | Hourihan et al. |
| 6,920,643 B2 | 7/2005 | McGlothlin et al. |
| 2002/0013963 A1 | 2/2002 | Nakamura et al. |
| 2002/0029402 A1 | 3/2002 | Yeh |
| 2003/0005508 A1 | 1/2003 | Hourihan et al. |
| 2003/0115659 A1 | 6/2003 | Williams |
| 2004/0031086 A1 | 2/2004 | Huynh et al. |
| 2004/0078867 A1 | 4/2004 | Herbert et al. |
| 2004/0107477 A1 | 6/2004 | Janssen |

* cited by examiner

DOUBLE-CUFFED CHEMOTHERAPY GLOVES

BACKGROUND

1. Technical Field

The present disclosure relates to protective gloves, and, in particular, relates to elastic gloves of the type used in administering chemotherapy drugs or other medically related practices.

2. Background of Related Art

Gloves and other personal protection equipment are often used in the medical and related fields to help prevent contamination between caregivers and patients. Disposable elastic gloves are often packaged as sterile or non-sterile products and used for surgical or examination purposes. The gloves are commonly fabricated from a thin elastomeric material such as latex, which can stretch to the shape of a hand to provide a very close fit and allow for an unimpaired tactile sense. This close fit feature can create difficulty in safely removing gloves that have become contaminated with biological or chemical hazards. To remove a glove, a clinician will often reach under the cuff with a finger or thumb of the opposite hand and peel the cuff toward the fingertips. Because the gloves are stretched taught against the wrist or forearm, even when extreme care is used this practice risks contact of the exterior surface of a glove with the skin and a resulting contamination of the skin.

One area in the medical field where skin contamination is a particular concern is the administering and mixing of chemotherapy drugs. Chemotherapy drugs are among the most potent and toxic (many have been identified as carcinogens) drugs available. on a milligram per milligram basis. Patients usually receive them only after they have been safely diluted, but clinicians often must handle these drugs in their undiluted form. Accordingly, clinicians typically wear protective gloves which are specifically adapted for this purpose. The Oncology Nursing Society (ONS) recommends that although the likelihood of permeation through these gloves is small, double gloves should be worn for all activities involving hazardous drugs to protect the clinician's hands from the contamination associated with removing the gloves. The National Institute for Occupational Safety and Health (NIOSH) also makes this recommendation so that a contaminated finger or thumb can be slipped between the gloves to remove the outer glove first without contacting the skin on the forearm. This practice will expose the clean inner glove which may then be used to remove the glove on the opposite hand.

Unfortunately, clinicians frequently fail to follow the recommendations set forth by the ONS and NIOSH due to the inconvenience of the additional time it takes to don an extra pair of gloves. Additionally, wearing two full sets of gloves detracts from the clinician's tactile sense. This impairment of dexterity makes it difficult to manipulate the small vials and glass ampoules in which chemotherapy drugs are often stored. Accordingly, there is a need for a glove that can be safely removed while not encroach on a clinician's ability to perform her job.

SUMMARY

The present disclosure describes a personal protection apparatus which may be worn on the hand to protect the wearer from contact with chemical or biological contaminants. In a preferred embodiment, the apparatus is a glove having a body formed from a material that is impermeable to the anticipated contaminants and includes a primary cuff at the proximal end. Affixed to the glove body at an annular attachment region encircling the glove body is a secondary cuff extending outwardly and proximally to a free end such that the wearer may grip the secondary cuff to remove the glove in the normal fashion without making contact with the skin on the forearm.

The secondary cuff may be attached to the glove body such that it is independent of the primary cuff and the attachment may be made entirely within a wrist portion of the glove. The proximal edges of the cuffs may be substantially spaced to facilitate grasping of secondary cuff with an opposite hand which may be contaminated. The glove body may be configured and dimensioned with materials selected such that the glove is suitable for use with common chemotherapy drugs.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1A:
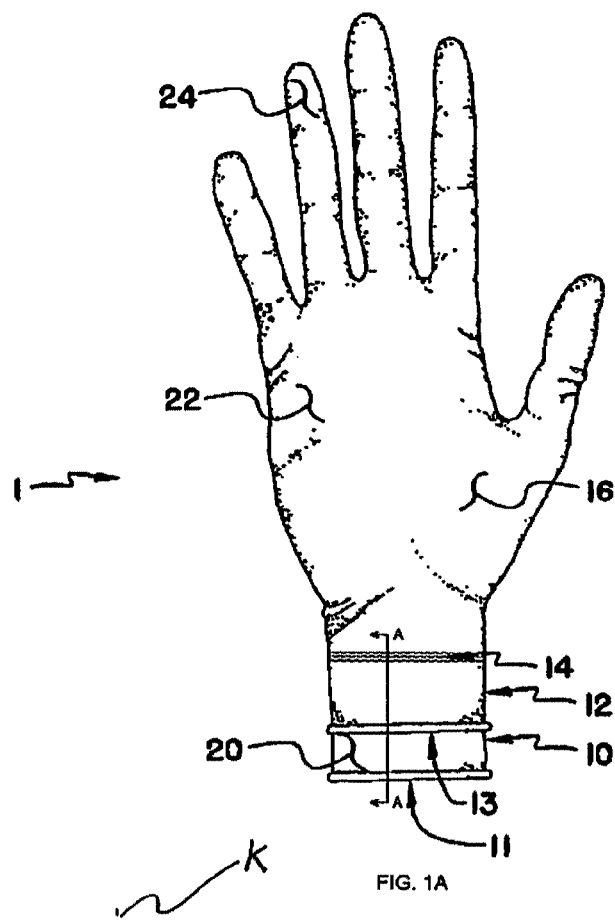
FIG. 1A is a front view of a hand cover constructed in accordance with the present disclosure.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views. In the discussion that follows, the term "clinician" refers to a doctor, nurse, pharmacist or other care provider and may include support personnel, while the term "wearer" is a more general term referring to any user of personal protection equipment described herein. The term "proximal" as is traditional will refer to the direction toward the wearer, while the term "distal" will refer to the direction away from the wearer.

Referring initially to FIG. 1A, an embodiment of the present disclosure is depicted as double-cuffed hand cover 1 including glove body 16, primary cuff portion 10, secondary cuff portion 12 and attachment region 14. Glove body 16 may be right handed, left handed or ambidextrous and is formed to approximate the shape of a human hand. Like all conventional gloves, it includes wrist portion 20 at the proximal end, metacarpal region 22 in the center and individual finger stalls 24 on the distal end. A body axis "k" runs through glove body 16 in a proximal to distal orientation. Glove body 16 is composed of a single layer of a flexible elastomeric material which is impermeable to the contaminants expected to be encountered while wearing hand cover 1. Impermeability to fluids common in the medical field is typically achieved by a thin gauged latex or natural rubber. In one embodiment, glove body 16 is formed from nitrile or neoprene.

Primary cuff 10 circumscribes proximal opening 40, which provides an entry point for a hand. Primary cuff 10 may be adapted for wrapping tightly around the wrist of a wearer to prevent penetration of contaminants between the glove and the wrist. Beaded proximal periphery 11 may be included as shown here, but the particular edge configuration of primary cuff 10 is not essential. Secondary cuff 12 is affixed to glove body 16 at attachment region 14 in the vicinity of wrist portion 20 and extends both radially outwardly relative to body axis "k" for a distance "m" and proximally or axially from attachment region 14 toward beaded edge 13 at its free end for a distance "b". Distance "b" is greater than distance "m" and is at least 1.5 times greater than distance "m". The particular edge configuration of the secondary cuff 12 is also not essential. Attachment region 14 encircles wrist portion 20 of glove body 16 so that secondary cuff 12 may resemble primary cuff 10, but, it is not essential that secondary cuff 12 be affixed to glove body 16 at each point within the region. Secondary cuff 12 may entirely circumscribe glove body 16, or alternatively, may extend around only a major portion, a substantial portion, or lesser portion of the circumference of glove body 16. The proximal most edges of primary and secondary cuffs 10, 12 are separated axially by grasping zone 34, which is broad enough that the wearer may comfortably rest a finger or thumb within grasping zone 34 without concern that the finger or thumb will protrude beyond primary cuff 10 to skin which may be unprotected. Grasping zone 34 provides a contact area the wearer may safely contact, possibly with the exterior of a contaminated glove, in order to remove double-cuffed hand cover 1. Secondary cuff 12 need not be formed from an impermeable material like glove body 16, but, preferably, maintains similar flexibility and elasticity characteristics.

Figure 1B:
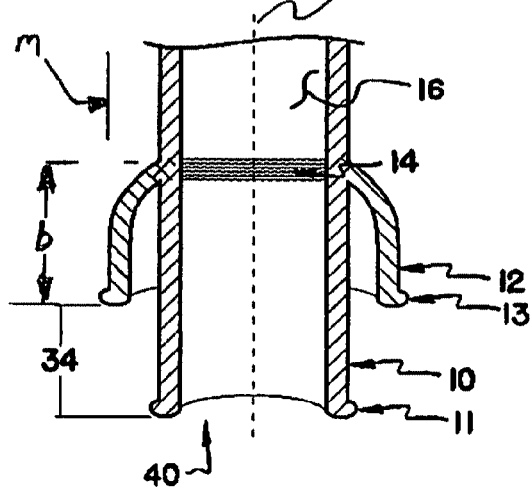
FIG. 1B is a section view of the hand cover taken along line A-A of FIG. 1A.

Secondary cuff 12 must be securely affixed to glove body 16 in a manner that does not interfere with its impermeability. Preferably, this is accomplished by co-molding a stout, generally cylindrically shaped flap of a thermoplastic elastomer entirely encircling glove body 16 at annular attachment region 14. Co-molding is a manufacturing process allowing for disparate materials to be formed together into a single integrated unit as seen in FIG. 1B by embedding one material into the other. The use of disparate materials may be advantageous for a variety of reasons. For example, since secondary cuff 12 does not contact the skin it may fit relatively loosely around glove body 16 to allow a finger or thumb to easily be inserted between primary and secondary cuffs 10, 12. Disparate materials may facilitate this design feature. Although co-molding is the preferred method for forming double-cuffed hand cover 1, any method may be used which is suitable for the material selected. For example, heat sealing, ultrasonic welding, or an appropriate adhesive may be appropriate in certain circumstances to attach secondary cuff 12. Alternatively, a single material may be used for both glove body 16 and secondary cuff 12 such that co-molding is not required. For example, glove body 16 including primary and secondary cuffs 10, 12 may be molded as a monolithically formed unit.

Figure 1C:
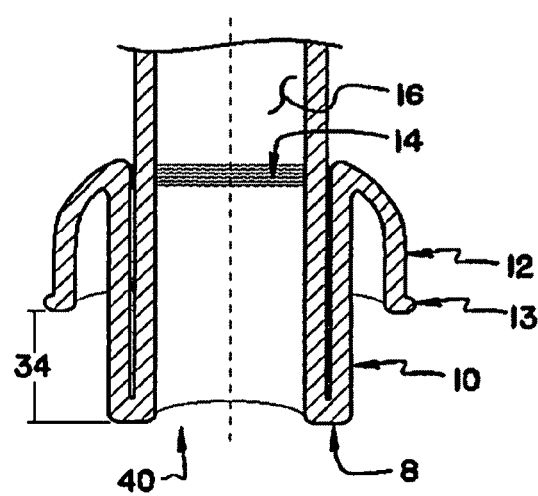
FIG. 1C is a view similar to 1B depicting an alternative configuration for the hand cover.

Although an independent secondary cuff 12 as shown in FIG. 1B is preferred, an alternative arrangement may be formed by making fold 8 in the primary cuff 10 as depicted in FIG. 1C. In this configuration, secondary cuff 12 is dependant on primary cuff 10 because of the additional layer of material forming primary cuff 10. The interdependence of primary and secondary cuffs 10, 12 may necessitate a permanent and secure attachment means be made in attachment region 14 to ensure double-cuffed hand covering 1 does not unfold into a single cuff arrangement.

Certain design features are preferable when gloves are adapted to be used by clinicians for handling common chemotherapy drugs. For example, the overall size may vary, but the overall length from the distal-most tip to the proximal opening is preferably approximately 12 inches so that the wrists may be fully protected. Although there are no formal requirements for the materials selected for chemotherapy gloves, a widely used test is ASTM F739, "Standard Method for Determining Resistance to Chemical Permeation under Conditions of Continuous Contact." Latex with a thickness of in the range of about 9 to about 18 mils at the fingertips has been found to work well, as has nitrile and neoprene with a thickness of about 8 to about 9 mils. The thickness of the material will depend on the level of protection required. For any material and protection level selected, the thickness is preferably minimized to allow the clinician to maintain an acute sense of feel.

Figure 2:
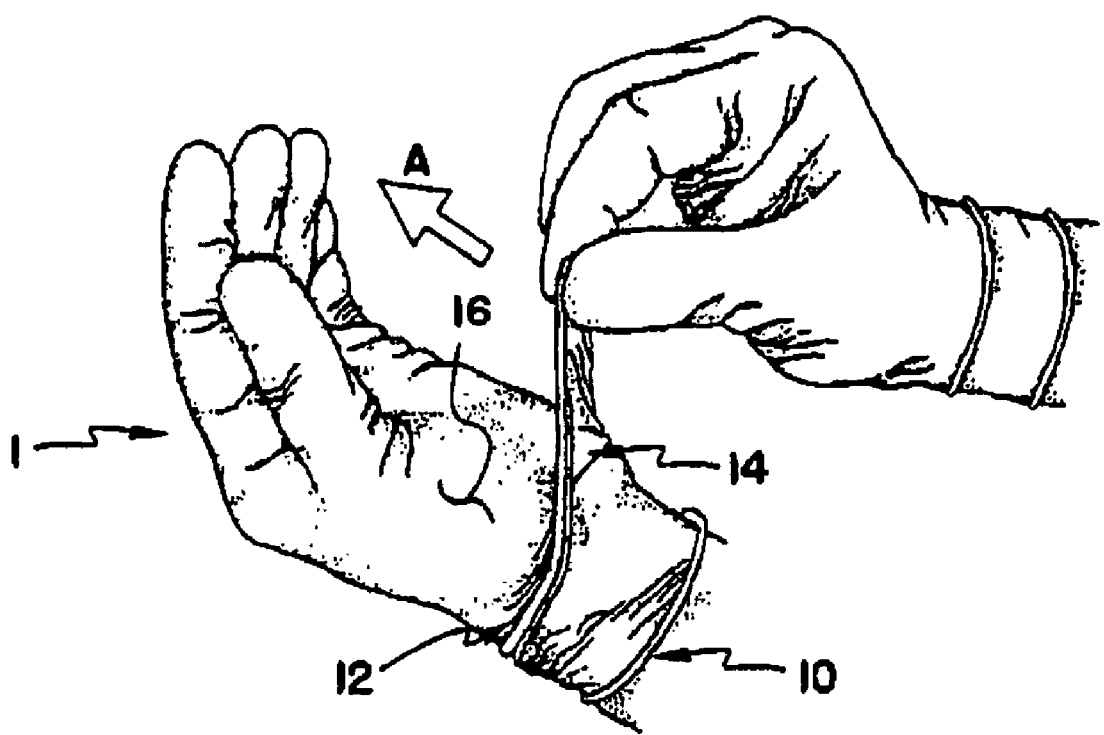
FIG. 2 is a pictorial view depicting the removal of the glove in FIG. 1A from the hand of a wearer.

Referring now to FIG. 2, removal of double-cuffed hand cover 1 will be described. To remove double-cuffed hand cover 1 from e.g., his/her left hand, the wearer positions a thumb e.g., of his/her right hand, adjacent grasping zone 34 and slides the thumb beneath secondary cuff 12 whereby secondary cuff 12 is between the thumb and a forefinger. An edge of secondary cuff 12 is lifted away from primary cuff 10 and pulled distally in the general direction of arrow "A" until double-cuffed hand cover 1 is completely removed from the wearer's hand, e.g., his/her left hand. In this way, the wearer can remove double-cuffed hand cover 1 in exactly the same manner as a conventional glove except that the skin on the wearer's forearm and hand is protected from accidental contact with the opposite hand by grasping zone 34 adjacent primary cuff 10. Because secondary cuff 12 encircles glove body 16, the wearer may also grasp secondary cuff 12 from a back side of the wrist, or at any point around glove body 16 for removal from the hand. Once double-cuffed hand cover 1 is removed from the first or left hand as described above, hand cover 1 on the opposite or right hand may be removed in the same manner, i.e. with the wearer's left hand positioned to grasp secondary cuff 12. However, in that the first or left hand is uncontaminated due to the double cuff arrangement, hand cover 1 on the remaining right hand may be removed, in the alternative, by positioning the wearer's thumb beneath primary cuff 10.

Finally, a hand cover with a double-cuffed arrangement need not incorporate glove body 16, as shown in the drawing figures, to provide accommodation for each individual finger. A hand body in the form of a mitten, accommodating only a thumb individually, may be used, or a simple sleeve covering the hand may be appropriate.

Although the foregoing disclosure has been described in some detail by way of illustration and example, for purposes of clarity or understanding, it will be obvious that certain changes and modifications may be practiced within the scope of the appended claims.

What is claimed is:

1. A personal protection apparatus adapted to be worn on a human hand for prevention of contact with chemical or biological contaminants, which camp rises:

a hand body defining a hollow enclosure terminating at an open entry end for permitting entry and reception of at least a hand of a wearer, the hand body defining a body axis;

a primary cuff adjacent to the open entry end; and a secondary cuff permanently attached to the hand body along an attachment region axially displaced from the open entry end along the body axis, the secondary cuff extending in a radial outward direction from the hand body relative to the body axis a radial spacing between the primary cuff and the secondary cuff to facilitate grasping of the secondary cuff and subsequent removal of the band body while substantially minimizing contamination of the hand during removal wherein the secondary cuff terminates in a free end, the free end being axially displaced from the open entry end of the hand body and radially displaced from the primary cuff.

2. The personal protection according to claim 1 wherein the secondary cuff is attached to the hand body along the attachment region, the attachment region at least partially circumscribing the hand body.

3. The personal protection apparatus according to claim 2 wherein the attachment region is dimensioned to circumscribe the hand body.

4. The personal protection apparatus according to claim 1 wherein the primary cuff has an axial length along the body axis sufficient to define a contact area between the open entry end of the hand body and the free end of the secondary cuff.

5. The personal protection apparatus according to claim 4 wherein the primary cuff is dimensioned to enclose a wrist area of the wearer.

6. The personal protection apparatus according to claim 1 wherein the free end of the secondary cuff includes a peripheral bead.

7. The personal protection apparatus according to claim 6 wherein the primary cuff includes a peripheral bead.

8. The personal protection apparatus according to claim 1 wherein the primary cuff and the secondary cuff comprise a monolithic unit with the hand body.

9. The personal protection apparatus according to claim 1 wherein the hand body comprises a single layer of an impermeable elastomeric material.

10. The personal protection apparatus according to claim 1 wherein the hand body comprises an impermeable material.

11. The personal protection apparatus according to claim 10 wherein impermeable material includes a latex material, the latex material having a thickness ranging from about 9 mils to about 18 mils.

12. The personal protection apparatus according to claim 10 wherein impermeable material includes nitrile.

13. The personal protection apparatus according to claim 10 wherein impermeable material includes neoprene.

14. The personal protection apparatus according to claim 1 wherein the hand body is in the general shape of a glove.

\* \* \* \* \*